US010094936B2

(12) United States Patent
Battyani (10) Patent No.: US 10,094,936 B2
(45) Date of Patent: Oct. 9, 2018

(54) X-RAY ANALYTICAL INSTRUMENT WITH IMPROVED CONTROL OF DETECTOR COOLING AND BIAS SUPPLY

(71) Applicant: Marc Battyani, Arlington, MA (US)

(72) Inventor: Marc Battyani, Arlington, MA (US)

(73) Assignee: OLYMPUS SCIENTIFIC SOLUTIONS AMERICAS INC., Waltham, MA (US)

( * ) Notice: Subject to any disclaimer, the term of this patent is extended or adjusted under 35 U.S.C. 154(b) by 400 days.

(21) Appl. No.: 14/931,921

(22) Filed: Nov. 4, 2015

(65) Prior Publication Data

US 2017/0123075 A1  May 4, 2017

(51) Int. Cl.
*G01T 1/24* (2006.01)
*G01T 1/175* (2006.01)
*G01N 23/223* (2006.01)

(52) U.S. Cl.
CPC ........... *G01T 1/175* (2013.01); *G01N 23/223* (2013.01); *G01N 2223/3103* (2013.01)

(58) Field of Classification Search
CPC .................. G01T 1/175; G01T 23/223; G01T 2223/3103

USPC ....................................................... 250/370.15
See application file for complete search history.

(56) References Cited

U.S. PATENT DOCUMENTS

2008/0001884 A1* 1/2008 Eames .................. G01T 1/1644
345/92
2014/0091228 A1* 4/2014 Yamakawa ............... G01T 1/24
250/370.09

* cited by examiner

*Primary Examiner* — David Porta
*Assistant Examiner* — Meenakshi Sahu
(74) *Attorney, Agent, or Firm* — C. Tricia Liu; Robert Kouim (57) ABSTRACT

Disclosed is a circuit for controlling the temperature and the bias voltage of a detector used by an X-ray analytical instrument. The circuit uses a single common reference voltage for the temperature measurement and for all the ADCs and DACs in the circuit, resulting in reduced drift and improved reproducibility of detector temperature and bias voltage. ADCs with a larger number of bits are used to produce precision values of the temperature, the bias voltage, and their respective setpoints. The setpoints are digitally varied until the precision setpoint values correspond to desired values of temperature and bias setpoints.

20 Claims, 6 Drawing Sheets

X-RAY ANALYTICAL INSTRUMENT WITH IMPROVED CONTROL OF DETECTOR COOLING AND BIAS SUPPLY

FIELD OF THE INVENTION

The present invention relates to control of detectors used in X-ray fluorescence (XRF) measurement systems, and more particularly to a circuit which enhances detector stability by using a single reference voltage to improve control of detector temperature and bias voltage.

BACKGROUND OF THE INVENTION

XRF detectors are usually energy dispersive, with each incident X-ray producing a pulse whose charge is proportional to the energy of the X-ray. The detector electronics is designed to convert the pulses from multiple X-rays into a spectrum, which is a plot of X-ray energies vs the number of X-rays received with that energy. Such a spectrum will exhibit peaks at energies which correspond to the characteristic X-ray energies of elements within the sample being measured. The position, magnitude and width of the peaks are critical parameters enabling identification of the elements in the sample and determination of their concentration.

In order to ensure that test results are accurate and repeatable, it is important to avoid electronic drift of signals from the detector. Signal drift will result in X-rays of the same energy being assigned a different energy in the spectrum at different measurement times. The signal drift may cause misidentification of elements and/or errors in measurement of their concentration. There are two detector parameters whose stability is particularly important for avoiding signal drift: these are the detector temperature and the detector bias voltage.

XRF detectors are usually cooled below room temperature by means of a cooling unit which is thermally coupled with the detector body. Maintaining accurate control of the cooling unit so that the detector temperature does not drift is essential to avoid signal drift.

XRF detectors require application of one or more bias voltages. In the present disclosure, reference may be made to components for control of a single bias voltage, but it is to be understood that whenever bias voltage is referred to in the singular, similar components may be used to maintain control of multiple bias voltages, and such components and the use of multiple bias voltages are all within the scope of the present disclosure.

Maintaining accurate control of the bias voltage regulator, ensuring that the bias voltage does not drift, is essential to avoid signal drift.

Control of a cooling unit generally requires a temperature setpoint (usually a digital value), a digital-to-analog converter (DAC) to convert the setpoint to an analog signal, an analog temperature measurement signal, and a comparator producing an error signal of the temperature measurement relative to the setpoint. The error signal is then used as the control signal for the cooling unit.

Similarly, control of a bias voltage generally requires a bias voltage setpoint (usually a digital value), a DAC to convert the setpoint to an analog signal, an analog bias voltage measurement signal, and a comparator producing an error signal of the bias voltage measurement relative to the setpoint. The error signal is then used as the control signal for the regulator of the bias voltage supply.

The temperature measurement signal and the DACs each require an accurate and stable reference voltage. In existing practice, the reference voltage for the temperature measurement may be on the detector preamplifier printed circuit board (PCB), the reference voltage for the temperature setpoint DAC may be on the cooling unit control PCB, and the reference voltage for the bias voltage setpoint DAC may be on the bias voltage supply control PCB. This means that there may be three different voltage references, each with its own specific accuracy and drift, and the combined effect of uncertainty of the voltage references may cause significant degradation of the detector signal accuracy. Degradation of measured detector signal amplitude accuracy includes time dependent drift of the signal amplitude during a single measurement, drift of the signal amplitude between different measurements on the same instrument, and inconsistent measurements of the same or similar sample made on different instruments.

A further optional element for control of the temperature is use of an analog-to-digital converter (ADC) for converting the analog temperature measurement signal to a digital value for comparison with the temperature setpoint. Similarly, an ADC may be used to convert the analog bias voltage measurement signal to a digital value for comparison with the bias voltage setpoint. However, each of these ADCs also requires a voltage reference, and in existing practice the voltage references for the ADCs may be different from the voltage references for the temperature measurement and the DACs. This causes errors in the temperature and bias voltage setpoints, which result in still further inaccuracy and drift in the detector signal.

SUMMARY OF THE INVENTION

The purpose of the invention is to alleviate problems with existing practice, particularly with respect to the inaccuracy and drift in the detector signal amplitude due to use of multiple voltage references to control detector temperature and bias voltage.

One embodiment of the invention is a circuit for controlling a detector cooling power supply. The circuit comprises a single common reference voltage, with a temperature measurement, a DAC and an ADC all referenced to the same single common reference voltage.

A second embodiment of the invention is a circuit for controlling one or more detector bias voltages. The circuit comprises a single common reference voltage, with a bias DAC and one or more bias ADCs all referenced to the same single common reference voltage.

A third embodiment of the invention is a circuit for controlling both a detector cooling power supply and one or more detector bias voltages. The circuit comprises a single common reference voltage, with a temperature measurement, a temperature DAC, a bias DAC, a temperature ADC and one or more bias ADCs all referenced to the same single common reference voltage.

DETAILED DESCRIPTION OF PREFERRED EMBODIMENTS

Note that in the description below, the term "voltage" is used to designate analog signals, and the term "value" is used to designate digital quantities.

Figure 1:
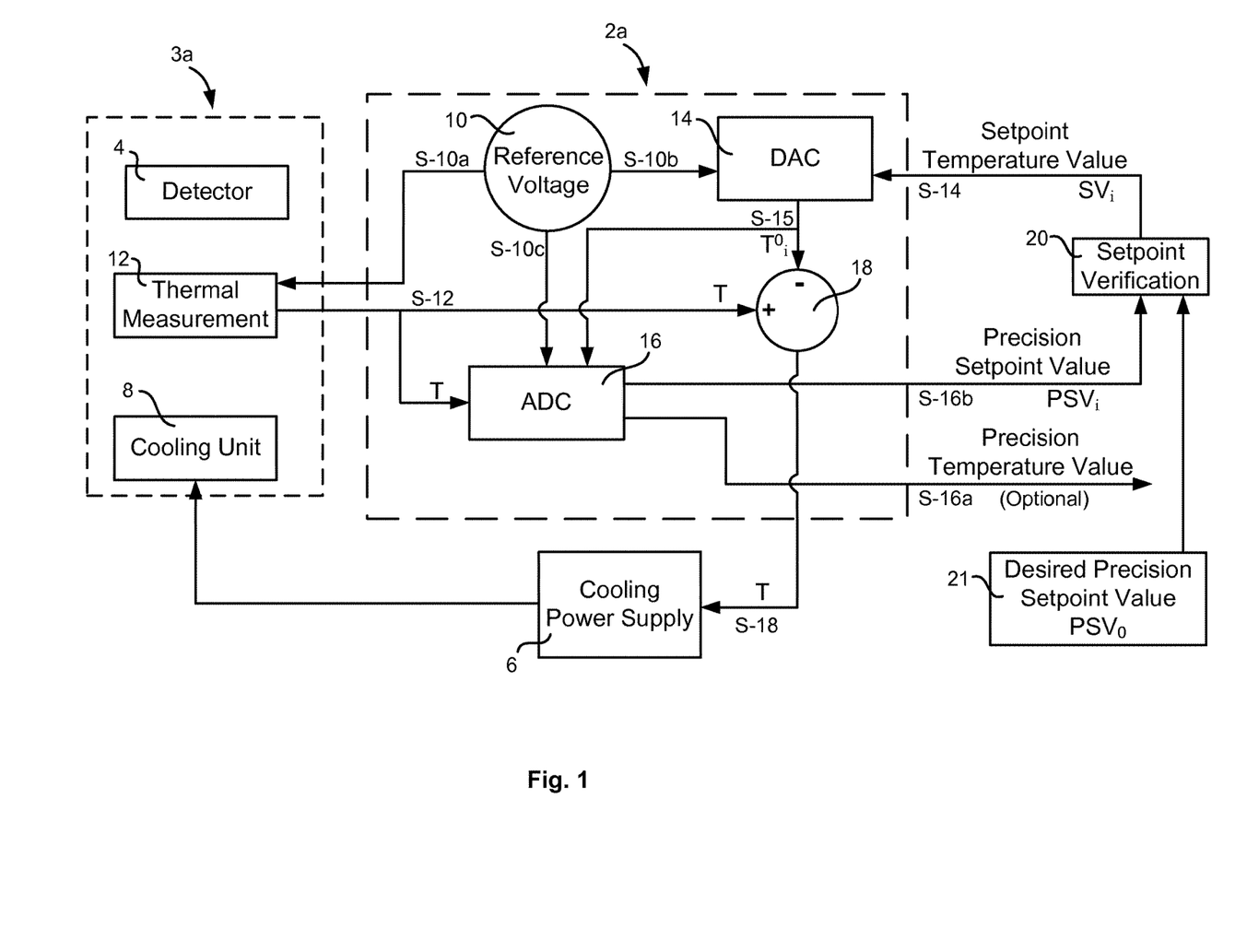
FIG. 1 is a schematic of a detector cooling control circuit according to the present disclosure.

FIG. 1 shows a detector temperature control circuit configured to regulate the temperature of an X-ray detector 4 typically used for an XRF analyzer. The temperature control circuit preferably includes a pre-amplifier circuit 2a and a detector assembly 3a. Detector assembly 3a includes X-ray detector 4, which may be of any type suitable for detecting X-rays, such as a silicon PIN detector or a silicon drift detector (SDD). Detector assembly 3a also includes a cooling unit 8 and a thermal measurement element 12 each of which is thermally coupled with detector 4. Pre-amplifier circuit 2a includes a reference voltage 10, a digital-to-analog converter or DAC 14, an analog-to-digital converter or ADC 16 and a comparator 18. Thermal measurement element 12 produces a temperature voltage S-12 which is a temperature measurement signal representative of the temperature T of the detector. As will later be further described in connection with FIG. 3, temperature voltage S-12 is based on reference voltage 10 via a connection S-10a. Temperature voltage S-12 is connected to a positive input of comparator 18, which is preferably a differential amplifier. A digital setpoint temperature value S-14 is input to DAC 14, and, using reference voltage 10 via a connection S-10b as its reference, DAC 14 produces a temperature setpoint voltage S-15. Temperature setpoint voltage S-15 is connected to a negative input of comparator 18, and comparator 18 produces an error voltage S-18, equal or proportional to the difference ΔT between temperature voltage S-12 and temperature setpoint voltage S-15. Error voltage S-18 is connected to a cooling power supply 6 which is configured to control cooling unit 8 such that error voltage S-18 is substantially zero.

Temperature voltage S-12 and temperature setpoint voltage S-15 are both also connected to the inputs of ADC 16. It is to be understood that ADC 16 comprises at least two independent analog-to-digital conversion channels. In fact ADC 16 may be a single chip with multiple independent channels or a single ADC with a switch at its input that operably selects one input signal or another. In order to carry out the digital conversion, each channel of ADC 16 requires a reference voltage which is supplied by a connection S-10c to reference voltage 10. ADC 16 produces a digital precision temperature value S-16a corresponding to analog input of temperature voltage S-12, and a digital precision setpoint value S-16b corresponding to analog input of temperature setpoint voltage S-15.

It should be noted that one of the novel aspects of the design of the temperature control circuit of FIG. 1 is that connections S-10a, S-10b and S-10c all share the same signal, which is reference voltage 10.

An alternative embodiment (not shown) of the temperature control circuit is to derive error voltage S-18 by digital subtraction of setpoint temperature value S-14 from precision temperature value S-16a. Cooling power supply 6 would then be configured to control cooling unit 8 such that the result of the digital subtraction is substantially zero. Comparator 18, which achieves the same result by analog subtraction, would not be required in this embodiment.

It should be noted that digital values S-14, S-16a and S-16b are available outside pre-amplifier 2a, and may be stored in a memory of a computer processor (not shown) which may be part of the XRF analyzer (also not shown).

It should also be noted that generally ADCs are commercially available with greater accuracy (larger number of digital bits) than DACs. In an exemplary embodiment herein presented, ADC 16 has 24 bits, while DAC 14 only has 16 bits. This means that temperature setpoint voltage S-15, which is an analog representation of digital setpoint temperature value S-14, is less accurate than precision setpoint value S-16b, which is a high precision digital representation of temperature setpoint voltage S-15. In other words, it is more accurate to measure an analog signal than to create that signal from a digital input.

Since precision setpoint value S-16b is the most accurate measurement of the actual setpoint voltage, it is advantageous to have a setpoint verification module 20, which is a software or other program configured as an iterative loop adjusting setpoint temperature value S-14 until precision setpoint value S-16b is equal to a desired precision setpoint value 21. Setpoint verification module 20 takes advantage of the scenario when ADC 16 is more accurate than DAC 14, and module 20 ensures that the setpoint as measured by ADC 16 is the desired setpoint. Setpoint verification module 20 may also be implemented with a hardware control feedback loop (not shown) and such hardware control is also within the scope of the present invention. The hardware control loop may be comprised of digital and/or analog circuitry. Use of setpoint verification module 20 is another novel aspect of the present disclosure by which the temperature setpoint is continuously verified relative to a single common reference voltage 10.

Figure 2:
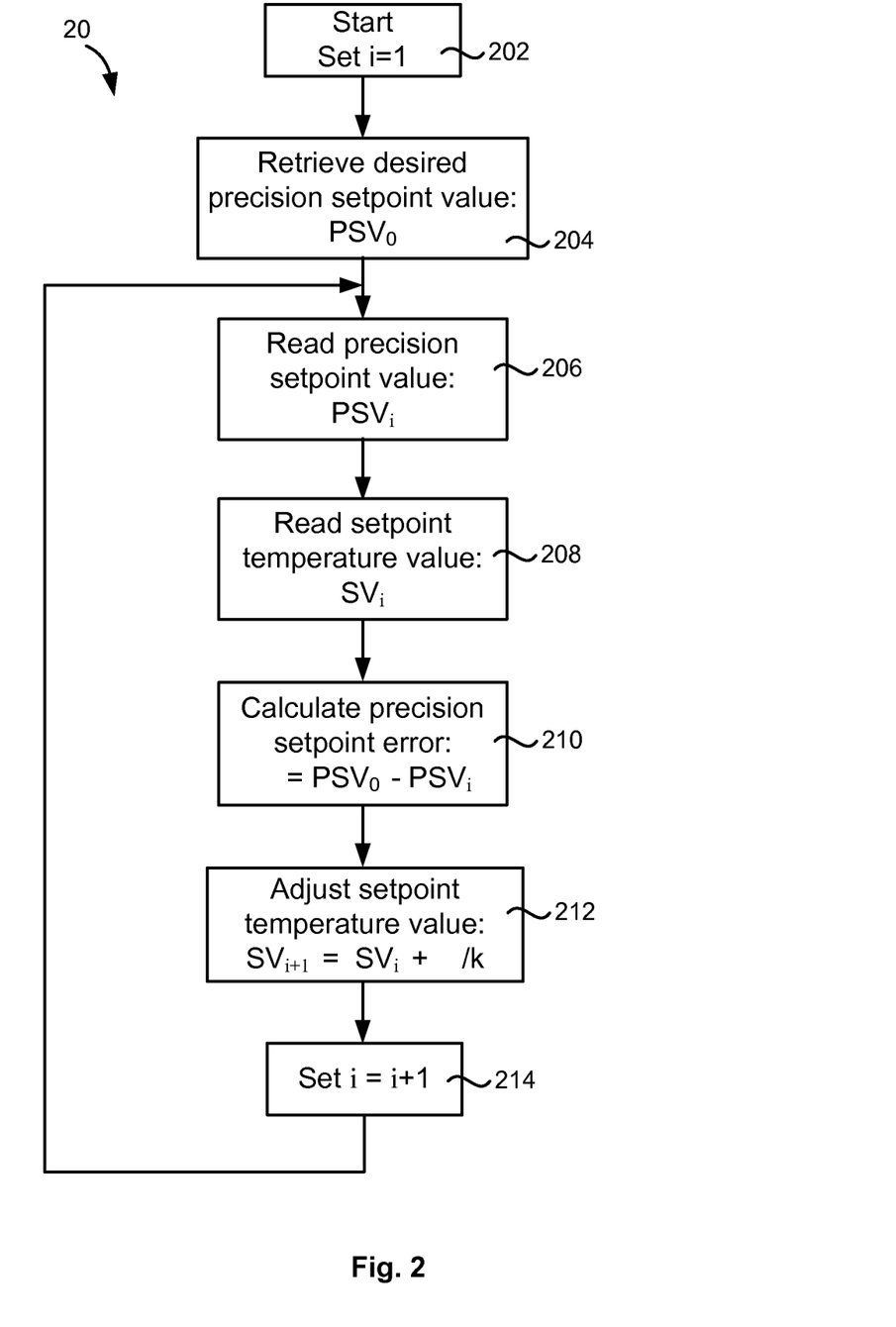
FIG. 2 is a schematic flow diagram of a setpoint verification module according to the present disclosure.

FIG. 2 shows an exemplary schematic flow diagram of iterative software setpoint verification module 20. In step 202 the software initializes the iteration by setting i=1, where i is the number of the iteration. In step 204 a desired precision setpoint value, $PSV_0$, is retrieved. $PSV_0$ is an operator input parameter which is stored in a computer memory which is accessible to a processor in which software setpoint verification module 20 operates. In step 206 an $i^{th}$ iteration of precision setpoint value, $PSV_i$, is read from precision setpoint value S-16b as shown in FIG. 1. In step 208 an $i^{th}$ iteration of the setpoint temperature value, $SV_i$, is read from setpoint temperature value S-14 as shown in FIG. 1. In step 210 an error in the precision setpoint value is calculated as $\Delta = PSV_0 - PSV_i$. In step 212 setpoint temperature value S-14 is adjusted to account for the error: $SV_{i+1} = SV_i + \Delta/k$, where k is a damping constant with a value greater than one, whose purpose is to prevent the feedback loop from oscillating. In step 214 the iteration number is incremented (i=i+1) and the iteration returns to step 206 and repeats.

Referring again to FIG. 1, it can be seen that, when $SV_i$ is adjusted by setpoint verification module 20, the input signal into DAC 14 changes, and therefore the DAC output, which is temperature setpoint voltage S-15, also changes to the next value of $T^o_i$, which is the $i^{th}$ iteration of the analog temperature setpoint $T^o$. Adjusted temperature setpoint voltage S-15 is input into ADC 16, which produces the next iteration, $PSV_i$, of precision setpoint value S-16b. Consequently, setpoint verification module 20 causes $PSV_i$ to rapidly converge to the value of $PSV_0$, at which point adjustments to $SV_i$ cease. However, module 20 continues to run to ensure that there is no system drift which may cause $PSV_i$ to diverge from the desired value $PSV_0$.

Having ensured a stable setpoint temperature value $SV_i$ and corresponding analog temperature setpoint $T°_i$, a stable temperature error signal $\Delta T$ is output from comparator 18 at error voltage S-18. Cooling power supply 6 then adjusts the power to cooling unit 8 in order to cause a temperature change at the detector to minimize the error signal $\Delta T$. After a delay due to thermal lag time within detector assembly 3*a*, stable detector temperature T as measured by thermal measurement element 12 is achieved, transmitted as temperature voltage S-12 to ADC 16, and read as stable precision temperature value S-16*a*.

Figure 3:
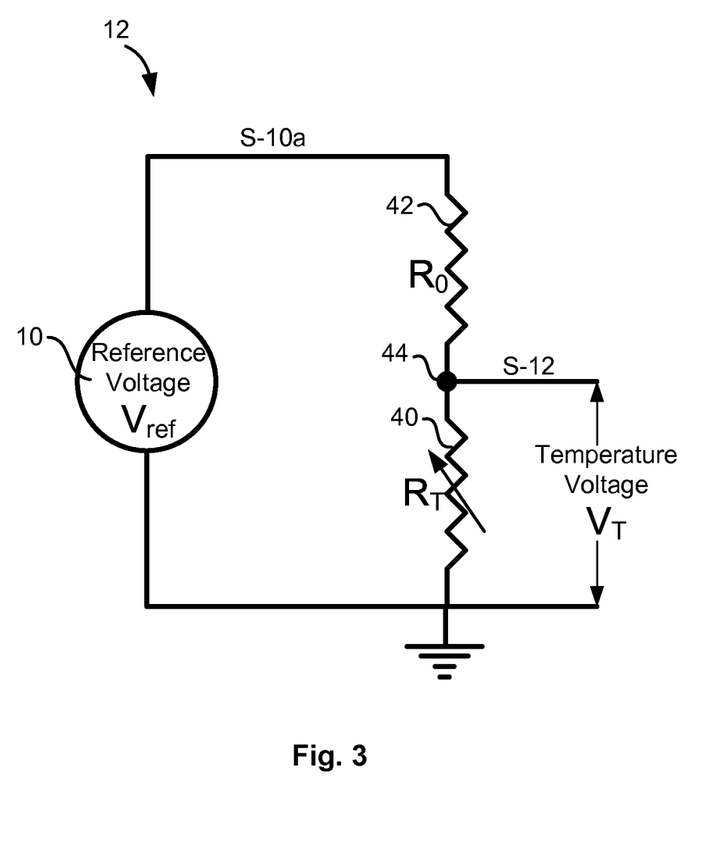
FIG. 3 is a schematic of a thermal measurement element according to the present disclosure.

FIG. 3 shows a circuit representation of thermal measurement element 12 which produces temperature voltage S-12 based on reference voltage 10. Reference voltage 10 is connected across a resistor 42 and a thermistor 40, which are connected to each other at a connection point 44. In an exemplary embodiment, thermistor 40 is a negative temperature coefficient resistor whose resistance depends on temperature in a known manner. Resistor 42 is a precision resistor having any convenient value, which in general is about the same as or somewhat less than the resistance of thermistor 40 at the detector operating temperature. The voltage at connection point 44 is temperature voltage S-12, and is given by $$V_T = \frac{R_T}{R_0 + R_T} V_{ref} \quad (1)$$

where $V_T$ is the temperature voltage at temperature T, $V_{ref}$ is the reference voltage, $R_0$ is the resistance of resistor 42 and $R_T$ is the resistance of thermistor 40 at temperature T. Thus it can be seen that temperature voltage S-12 is directly proportional to reference voltage 10, meaning that any change in reference voltage 10 due to drift results in a proportional change in temperature voltage S-12.

It should be noted that an important novel aspect of the present invention is detector temperature control using reference voltage 10 as a single reference for ADC 16, DAC 14 and thermal measurement element 12. A typical reference voltage unit may have a voltage of 2.5V±250 ppm. This means that in existing practice circuits using multiple reference units, the reference voltages of the ADC, DAC and thermal measurement element may differ by as much as 500 ppm and it will be difficult to attain reproducible temperature performance between different XRF analyzers in a manufacturing environment. On the other hand, when all components are using the same reference voltage, variations in the voltage are cancelled out, ensuring reproducibility of detector temperature from instrument to instrument. Similarly, the specification for drift of the reference voltage, typically±2 ppm, causes temperature drift in prior art instruments, whereas when all components are using the same reference voltage, the voltage drifts are cancelled out, thereby minimizing temperature drift.

It should also be noted that a further important novel aspect of the present invention is the use of setpoint verification module 20 to ensure that the temperature setpoint remains stable and equal to the desired setpoint.

Using a temperature control circuit according to the present disclosure, incorporating both single reference voltage 10 and setpoint verification module 20, long term detector temperature stability of less than±0.001° C. was achieved. In existing practice, detector stability is typically about±0.1° C., or about 100 times worse. Such improvement in temperature stability results in significant improvement in spectrum repeatability, thereby improving overall performance of the XRF analyzer.

Figure 4:
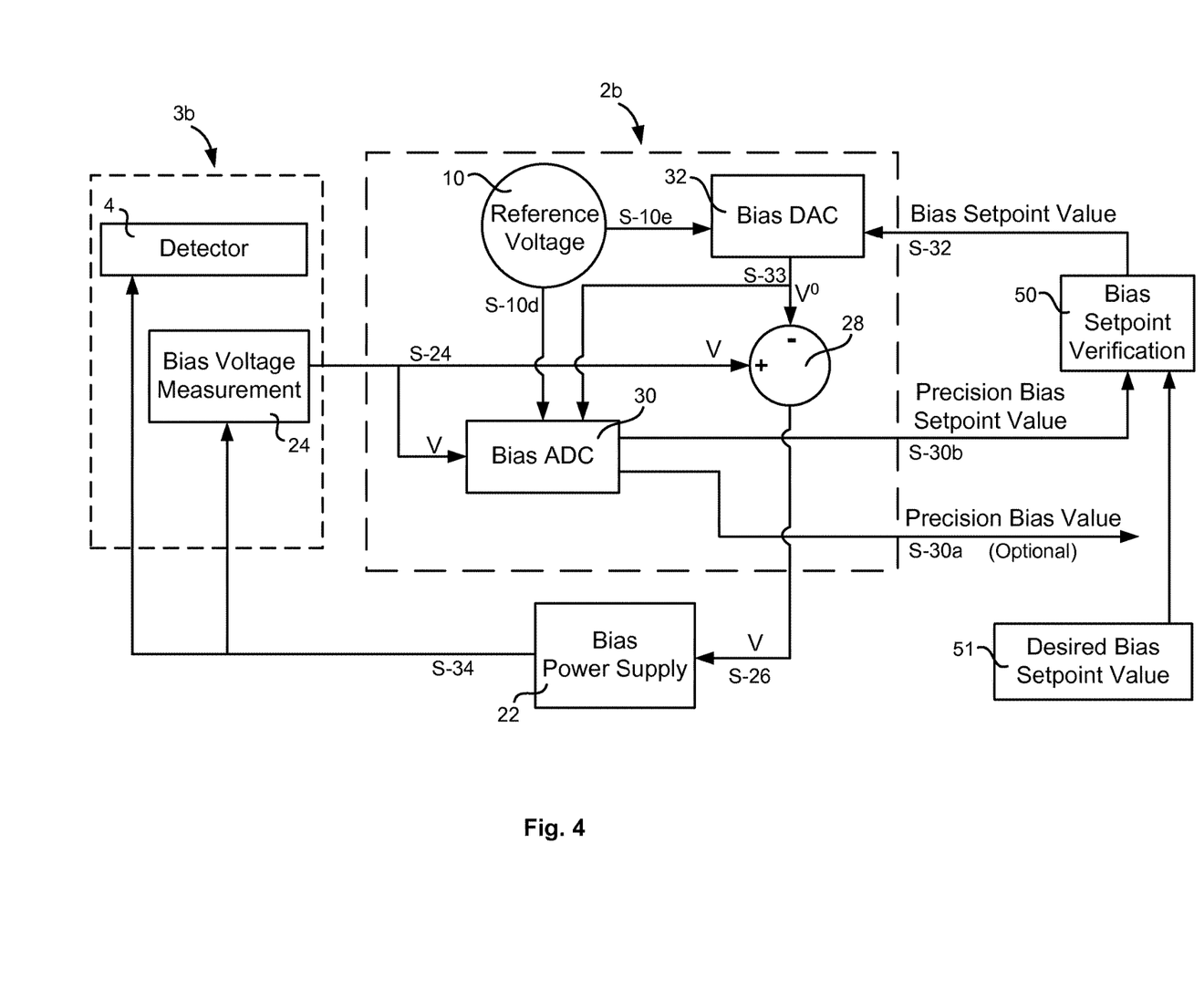
FIG. 4 is a schematic of a detector bias voltage control circuit according to the present disclosure.

Referring now to FIG. 4, in another embodiment of the present disclosure, a schematic diagram shows a bias control circuit for controlling the detector bias voltage, and including an alternative pre-amplifier circuit 2*b* and an alternative detector assembly 3*b*. The bias control circuit includes a bias power supply 22, producing a bias voltage S-34, which is supplied to detector 4 and to a bias voltage measurement unit 24. Detector assembly 3*b* includes detector 4 and bias voltage measurement unit 24. Pre-amplifier circuit 2*b* includes reference voltage 10, a bias DAC 32, a bias ADC 30 and a bias comparator 28. It is to be understood that ADC 30 comprises at least two independent analog-to-digital conversion channels. In fact ADC 30 may be a single chip with multiple independent channels or a single ADC with a switch at its input that operably selects one input signal or another.

Bias voltage measurement unit 24 produces a bias measurement voltage S-24, represented by the symbol V, and further described below in connection with FIG. 5. Bias measurement voltage S-24 is connected to a positive input of bias comparator 28. A digital bias setpoint value S-32 is input to bias DAC 32, and, using reference voltage 10 via connection S-10*e* as its reference, bias DAC 32 produces a bias setpoint voltage S-33, which is represented by the symbol $V^0$. Bias setpoint voltage S-33 is connected to a negative input of bias comparator 28, and bias comparator 28 produces a bias error voltage S-26, represented by the symbol $\Delta V$, which is the error between bias setpoint voltage S-33 and bias measurement voltage S-24. Bias error voltage S-26 is connected to bias power supply 22, which includes a voltage regulator (not shown) configured to control bias voltage S-34, such that voltage error $\Delta V$ is substantially zero.

Bias measurement voltage S-24 and bias setpoint voltage S-33 are both also connected to the inputs of bias ADC 30. Bias ADC 30 produces a digital precision bias value S-30*a* corresponding to analog input of bias measurement voltage S-24, and a digital precision bias setpoint value S-30*b* corresponding to analog input of bias setpoint voltage S-33. Bias ADC 30 uses reference voltage 10 as its reference via connection S-10*d*.

It should be noted that one of the novel aspects of the design of the bias control circuit in FIG. 4 is that connections S-10*d* and S-10*e* share a same signal, which is reference voltage 10 as reference voltage 10 is used as a common single reference.

When bias ADC 30 (24 bits in a preferred embodiment) is more accurate than bias DAC 32 (16 bits), it is advantageous to have a bias setpoint verification module 50, which operates for bias control in a manner analogous to operation of setpoint verification module 20 for temperature control as described in relation to FIG. 1. Bias setpoint verification module 50 is a software or hardware module configured as an iterative loop adjusting bias setpoint value S-32 until precision bias setpoint value S-30*b* is equal to a desired bias setpoint value 51. The hardware module may be comprised of digital and/or analog circuitry. The operative effect of bias setpoint verification module 50 on bias setpoint value S-32 is analogous to the operation of setpoint verification module 20 on setpoint temperature value S-14, as described in relation to FIGS. 1 and 2. Specifically, bias setpoint verification module 50 causes precision bias setpoint value S-30*b* to rapidly converge to the value of desired bias setpoint value 51. Use of bias setpoint verification module 50 is another novel aspect of the present disclosure by which the bias voltage setpoint is continuously verified relative to a single common reference voltage 10.

Figure 5:
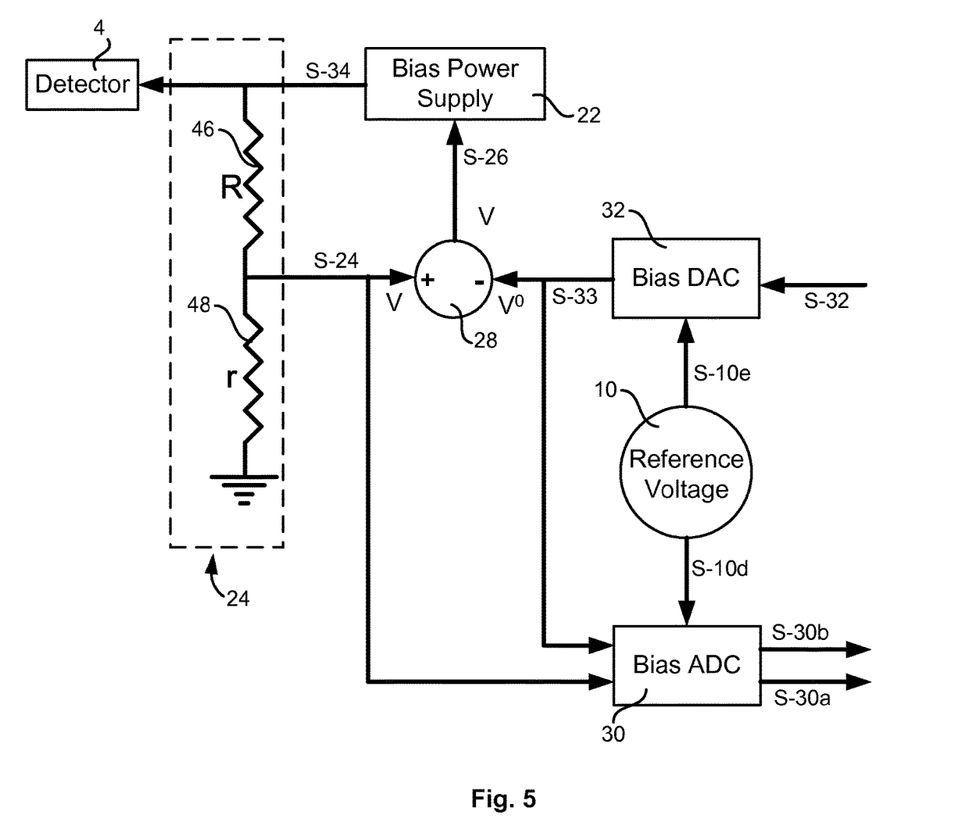
FIG. 5 is a schematic of a bias voltage measurement and control circuit according to the present disclosure.

FIG. 5 is a schematic of a circuit for providing detector bias voltage S-34 to detector 4 and for further providing bias measurement voltage S-24, which is representative of bias voltage S-34. It is understood that the circuit of FIG. 5 provides one bias voltage and one bias measurement voltage. In the event that the detector requires multiple bias voltages, multiple circuits according to FIG. 5 are required. Bias power supply 22 has an internal or external voltage regulator (not shown) which supplies detector 4 with regulated bias voltage S-34. For a PIN detector, bias power supply 22 typically delivers a maximum of approximately+190V, allowing regulated bias voltage S-34 to be between+130V and+180V as required by the PIN detector. For an SDD detector, three different bias voltages may be required and they may all be delivered by one power supply of approximately−190V, supplying three different voltage regulators delivering between−130V and−180V to a first electrode, between−50V and−90V to a second electrode, and between−15V and−25V to a third electrode.

Bias voltage S-34 is too large for convenient use with a comparator or an ADC. In general, the comparator or ADC input voltage should be less than the voltage of reference voltage 10, which is typically about 2.5V. Bias measurement voltage S-24 is therefore produced by bias voltage measurement unit 24, which comprises a larger resistor 46 and a smaller resistor 48 configured to accurately reduce bias voltage S-34 by a known amount depending on the values of the two resistors:

$$S24 = \frac{r}{R+r} S34 \tag{2}$$

where R is the resistance of resistor 46, and r is the resistance of resistor 48, and r/(R+r) is a divider ratio for accurately reducing bias measurement voltage S-24 relative to bias voltage S-34. Resistors 46 and 48 should be precision (<0.1%) resistors with low temperature drift characteristics. Choice of their resistance values depends on the bias voltage being supplied and the requirement that bias measurement voltage S-24 should be between 0V and 2.5V. For example, if the requirement for bias voltage S-34 is 180V, then R=2 MΩ and r=20 kΩ would provide a convenient 1.78V for bias measurement voltage S-24.

Referring back to FIG. 4, it should be noted that a further important novel aspect of the present invention is control of detector bias using a single reference voltage 10 as reference for both bias ADC 30 and bias DAC 32.

Yet another important novel aspect of the present invention is use of bias setpoint verification module 50 in the bias control circuit, ensuring that the bias setpoint remains stable and equal to the desired bias setpoint.

Using a bias control circuit according to the present disclosure, incorporating both single reference voltage 10 and bias setpoint verification module 50, long term detector bias stability between±0.01V and±0.1V was measured. In the existing practice, detector bias stability is typically about±1V, or about 10 to 100 times worse. Such improvement in bias voltage stability results in significant improvement in spectrum repeatability, thereby improving overall performance of the XRF analyzer.

Figure 6:
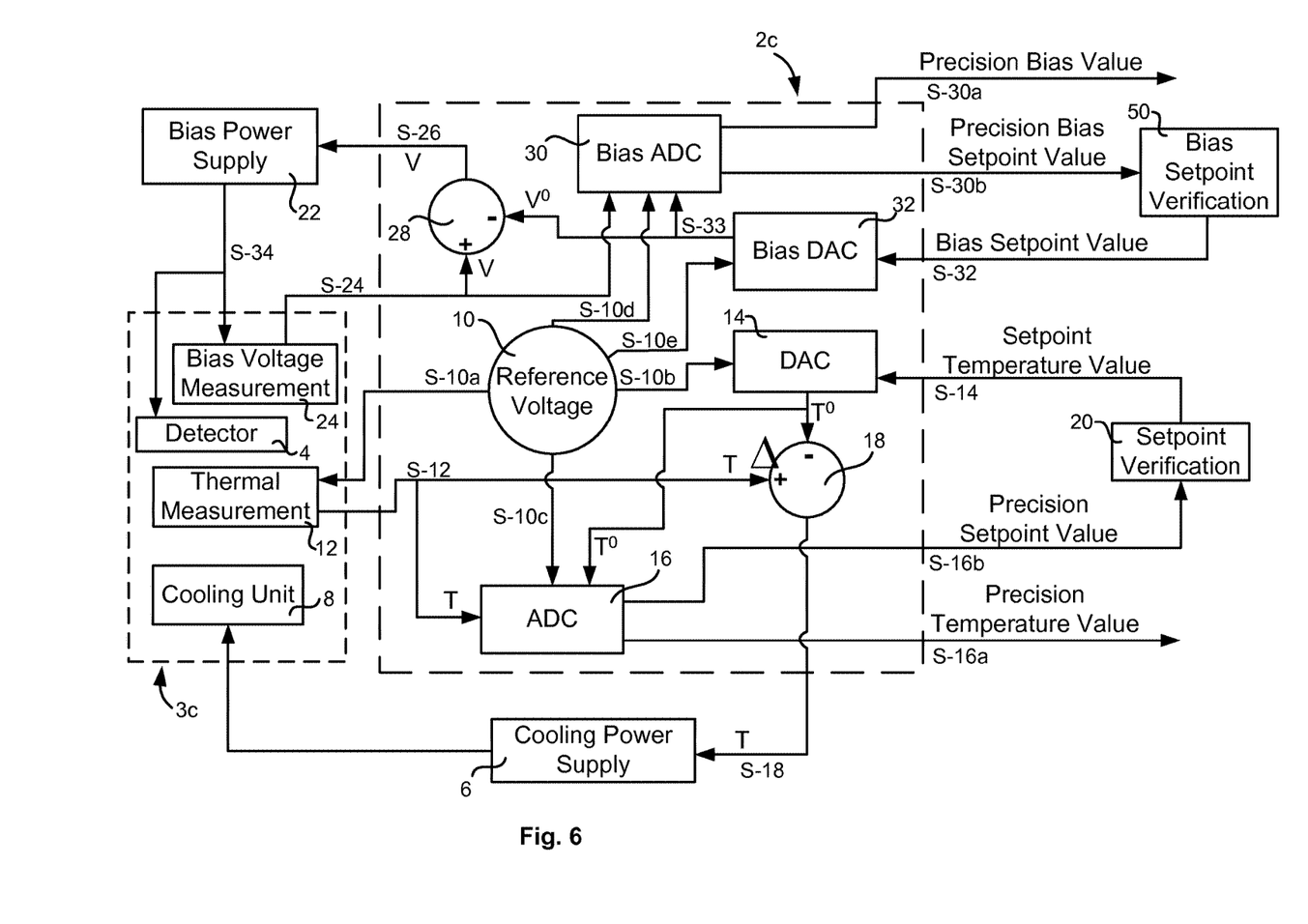
FIG. 6 is a schematic of a combined detector cooling and bias voltage control circuit according to the present disclosure.

Referring now to FIG. 6, a schematic diagram shows a combined temperature and bias control circuit for controlling both the detector temperature and the detector bias voltage, and including a pre-amplifier circuit 2c and a detector assembly 3c. The temperature and bias control circuit combines all the elements and functionality incorporated in the temperature control circuit as previously described in connection with FIG. 1 and the bias control circuit as previously described in connection with FIG. 4

Referring again to FIG. 6, it should be noted that a further important novel aspect of the present invention is control of both detector temperature and detector bias using a single reference voltage 10 as reference for ADC 16, DAC 14, thermal measurement element 12, bias ADC 30 and bias DAC 32. In the temperature control circuit, common reference voltage 10 is used for temperature control components, in the bias control circuit, common reference voltage 10 is used for bias control components, while in the temperature and bias control circuit of FIG. 6, common reference voltage 10 is used for both temperature control and bias control components. Use of common reference 10 for both temperature and bias control in the temperature and bias control circuit contributes further to the stability of the spectrum from the XRF analyzer, since the electronic drift of signals from the detector may be caused by either temperature drift or bias voltage drift.

Yet another important novel aspect of the present invention is use of both setpoint verification module 20 and bias setpoint verification module 50 in the temperature and bias control circuit. Setpoint verification module 20 ensures that the temperature setpoint remains stable and equal to the desired temperature setpoint. At the same time bias setpoint verification module 50 ensures that the bias setpoint remains stable and equal to the desired bias setpoint.

Although the present invention has been described in relation to particular embodiments thereof, it can be appreciated that various designs can be conceived based on the teachings of the present disclosure, and all are within the scope of the present disclosure.

What is claimed is:

1. A circuitry for controlling a cooling power supply providing cooling power to a cooling unit of a detector of an X-ray analyzer, the circuitry comprises:
    a thermal measurement element producing a temperature measurement of the detector and subsequently a temperature voltage,
    a pre-amplifier circuit providing a control signal for controlling the cooling power, the pre-amplifier circuit further comprises:
        a single common reference element providing a common reference voltage,
        a digital-to-analog converter (DAC) configured to produce a setpoint voltage based on a pre-determined setpoint temperature value,
        an analog-to-digital converter (ADC) configured to digitize the temperature voltage and the setpoint voltage and produce a precision setpoint value, wherein the precision setpoint value is used to produce an adjusted setpoint voltage,
        a comparator producing a differential value between the temperature voltage and the adjusted setpoint voltage wherein the differential value is used as a basis for the control signal, wherein the common reference voltage is referenced by the thermal measurement, the DAC and the ADC.

2. The circuitry of claim 1 wherein the ADC is referenced to the reference voltage.

3. The circuitry of claim 1 wherein the DAC is referenced to the reference voltage.

4. The circuitry of claim 1 wherein the thermal measurement element is referenced to the reference voltage.

5. The circuitry of claim 1 wherein the thermal measurement element comprises:
   a thermistor electrically connected to ground at a thermistor first end and to a connection point at a thermistor second end,
   a precision resistor electrically connected to the connection point at a resistor first end and to the reference voltage at a resistor second end, and,
   wherein the temperature voltage is measured at the connection point.

6. The circuitry of claim 1, wherein the pre-amplifier circuit is assembled on at least one circuit board.

7. The circuitry of claim 1, wherein the comparator is a differential amplifier.

8. The circuitry of claim 1 wherein the ADC and the DAC each has a respective number of bits, and the ADC has a larger number of bits than the DAC.

9. The circuitry of claim 1 wherein the ADC is used to produce a precision temperature value.

10. The circuitry of claim 1 wherein the temperature voltage and the temperature setpoint voltage are both provided to the ADC as respective inputs, and the ADC comprises at least two independent analog-to-digital conversion channels, each used for the respective input.

11. The circuitry of claim 1 further comprises a setpoint verification module and the pre-amplifier circuit is electronically coupled with the verification module.

12. The circuitry of claim 11 wherein the verification module is an executable computer program code residing on a data processing unit.

13. The circuitry of claim 12 wherein the verification module is configured to execute iteratively for each iteration number of i, wherein i=1, 2, . . . , the steps of the program code including:
   retrieving a desired precision temperature value $PSV_0$, from the data processing unit,
   retrieving an $i^{th}$ iteration of the precision setpoint value, $PSV_i$,
   retrieving an $i^{th}$ iteration of the setpoint temperature value, $SV_i$,
   calculating a digital precision setpoint error, $\Delta$, given by $\Delta = PSV_0 - PSV_i$, wherein the differential value is the analog equivalent of the digital precision setpoint error,
   setting the adjusted setpoint temperature value based on the precision setpoint error, thereby producing an $(i+1)^{th}$ iteration, $SV_{i+1}$, of the setpoint temperature value,
   continuing the iteration with the next value of i.

14. A circuitry for providing a bias voltage via a bias power supply to a detector of an X-ray analyzer, the circuitry comprises:
   a bias voltage measurement element producing a bias measurement voltage,
   a pre-amplifier circuit providing a control signal for controlling the bias power supply, the pre-amplifier circuit further comprises:
      a single common reference element providing a common reference voltage,
      a bias digital-to-analog converter (DAC) configured to produce a setpoint voltage based on a pre-determined bias setpoint value and the reference voltage,
      a bias analog-to-digital converter (ADC) configured to digitize the bias measurement voltage and the bias setpoint voltage and produce a precision bias setpoint value, wherein the precision bias setpoint value is used to produce an adjusted bias setpoint voltage,
      a comparator producing a differential value between the bias voltage and the adjusted bias setpoint voltage wherein the differential value is used as a basis for the control signal, wherein the common reference voltage is referenced by the bias DAC and the bias ADC.

15. The circuitry of claim 14 wherein the precision bias setpoint value is used to adjust the bias setpoint value, which is further used to produce an adjusted bias setpoint voltage.

16. The circuitry of claim 14 wherein the bias measurement voltage is equal to the detector bias voltage multiplied by a divider ratio.

17. The circuitry of claim 16 wherein the divider ratio is equal to the resistance of a first smaller resistor divided by the sum of the resistances of the first resistor and a second larger resistor.

18. The circuitry of claim 14 wherein the bias voltage is determined by a bias regulator which is controlled by the control signal, and wherein the differential value is used as the control signal.

19. The circuitry of claim 14, further comprises a bias setpoint verification module and the pre-amplifier circuit is electronically coupled with the bias setpoint verification module.

20. The circuitry of claim 19 wherein the verification module is an executable computer program code residing on a data processing unit.

* * * * *